US012592316B2

(12) United States Patent
Tremblay et al.

(10) Patent No.: US 12,592,316 B2
(45) Date of Patent: Mar. 31, 2026

(54) DIAGNOSTIC METHODS AND SYSTEMS USING SOUND DETECTION

(71) Applicant: Fresenius Medical Care Holdings, Inc., Waltham, MA (US)

(72) Inventors: John E. Tremblay, Bolton, MA (US); Harvey Cohen, Newton, MA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 107 days.

(21) Appl. No.: 17/881,198

(22) Filed: Aug. 4, 2022

(65) Prior Publication Data

US 2024/0047059 A1 Feb. 8, 2024

(51) Int. Cl.
G16H 40/63 (2018.01)
A61M 1/26 (2006.01)
A61M 1/28 (2006.01)
A61M 1/36 (2006.01)

(52) U.S. Cl.
CPC ............ G16H 40/63 (2018.01); A61M 1/267 (2014.02); A61M 1/28 (2013.01); A61M 1/3656 (2014.02); *A61M 2205/3375* (2013.01); *A61M 2205/3553* (2013.01); *A61M 2205/581* (2013.01); *A61M 2205/583* (2013.01)

(58) Field of Classification Search
CPC ......... G16H 40/63; A61M 1/267; A61M 1/28; A61M 1/3656; A61M 2205/3375; A61M 2205/3553; A61M 2205/581; A61M 2205/583
See application file for complete search history.

(56) References Cited

U.S. PATENT DOCUMENTS

| | | | |
|---|---|---|---|
| 9,095,314 B2 * | 8/2015 | Osorio | ............... A61N 1/37258 |
| 10,976,730 B2 | 4/2021 | Deshpande et al. | |
| 11,965,859 B1 | 4/2024 | Jenkins et al. | |
| 2006/0064037 A1 | 3/2006 | Shalon et al. | |
| 2006/0135907 A1 * | 6/2006 | Remde | .............. A61M 5/16831 604/67 |
| 2008/0018435 A1 * | 1/2008 | Brown | ................... G16H 40/20 340/286.07 |
| 2009/0082676 A1 * | 3/2009 | Bennison | ............ A61M 1/3656 600/462 |
| 2011/0021967 A1 | 1/2011 | Heide et al. | |
| 2014/0018637 A1 * | 1/2014 | Bennett | .............. H04L 43/0817 607/51 |

(Continued)

FOREIGN PATENT DOCUMENTS

| | | |
|---|---|---|
| EP | 2988105 | 2/2016 |
| EP | 3861307 | 8/2021 |

(Continued)

OTHER PUBLICATIONS

JP-2018179863 machine translation. (Year: 2018).*

(Continued)

*Primary Examiner* — Mamon Obeid
*Assistant Examiner* — Malak M Nasser
(74) *Attorney, Agent, or Firm* — Fish & Richardson P.C.

(57) ABSTRACT

A method of monitoring a medical treatment device includes detecting a sound of the medical treatment device with a detection device, determining whether the sound is an irregular sound, and deploying an intervention upon determining that the sound is the irregular sound.

23 Claims, 9 Drawing Sheets

(56)                References Cited

U.S. PATENT DOCUMENTS

| | | | | |
|---|---|---|---|---|
| 2014/0121845 A1* | 5/2014 | Mueller | ................. | G16Z 99/00 |
| | | | | 700/282 |
| 2014/0188516 A1* | 7/2014 | Kamen | ................. | G16H 20/10 |
| | | | | 705/3 |
| 2020/0219527 A1 | 7/2020 | Kogan et al. | | |
| 2020/0234818 A1 | 7/2020 | Usvyat et al. | | |
| 2020/0356898 A1 | 11/2020 | Claussen et al. | | |
| 2022/0026879 A1 | 1/2022 | Kale | | |
| 2023/0064906 A1* | 3/2023 | Jamieson | .............. | G08B 21/02 |
| 2024/0044747 A1 | 2/2024 | Pickering et al. | | |

FOREIGN PATENT DOCUMENTS

| | | | | | |
|---|---|---|---|---|---|
| JP | 2018179863 | A | * | 11/2018 | |
| JP | 2020-185124 | | | 11/2020 | |
| WO | WO 2009/042577 | | | 4/2009 | |
| WO | WO 2017/112591 | | | 6/2017 | |
| WO | WO 2018/184833 | | | 10/2018 | |
| WO | WO-2020036091 | A1 | * | 2/2020 | ............ G16H 40/40 |
| WO | WO-2023178161 | A2 | * | 9/2023 | |

OTHER PUBLICATIONS

English Translation (Year: 2020).*
International Search Report and Written Opinion in International Appln. No. PCT/US2023/029201, mailed Nov. 27, 2023, 13 pages.
International Preliminary Report on Patentability in International Appln. No. PCT/US2023/029201, mailed Feb. 13, 2025, 7 pages.

* cited by examiner

132

PD cassette and pump

700

Detect sound

702

Determine sound signature

704

Determine that detected sound signature matches predetermined sound signature

706

Determine intervention

708

Determine phase of treatment

710

Deploy intervention

712

DIAGNOSTIC METHODS AND SYSTEMS USING SOUND DETECTION

TECHNICAL FIELD

The present disclosure relates to diagnostic methods and systems using sound detection.

BACKGROUND

Dialysis is a treatment used to support a patient with insufficient renal function. The two principal dialysis methods are hemodialysis and peritoneal dialysis.

During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), a patient's peritoneal cavity is periodically infused with dialysis solution or dialysate. The membranous lining of the patient's peritoneum acts as a natural semi-permeable membrane that allows diffusion and osmosis exchanges to take place between the solution and the blood stream. These exchanges across the patient's peritoneum, like the continuous exchange across the dialyzer in HD, result in the removal of waste products, including solutes like urea and creatinine, from the blood, and regulate the levels of other substances, such as sodium and water, in the blood.

Many PD machines are designed to automatically infuse, dwell, and drain dialysate to and from the patient's peritoneal cavity. The treatment typically lasts for several hours, often beginning with an initial drain procedure to empty the peritoneal cavity of used or spent dialysate. The sequence then proceeds through the succession of fill, dwell, and drain phases that follow one after the other. Each phase is called a cycle.

SUMMARY OF THE INVENTION

Certain methods and systems described herein enable the ability to diagnose a mechanical issue upon detecting unique sounds that occur surrounding a patient's treatment. Sounds that occur before treatment, during treatment, or post treatment can provide insights into machine conditions or treatment events that could be aided by automated, real-time interventions or trigger certain needed clinician or technical support. For example, home therapies can especially benefit from remote and automated insight into patient treatments being performed, e.g., given the more limited experience patients typically have with their dialysis equipment.

A range of diagnostics can be harvested from audible sounds within the proximity of a patient undergoing therapy. Each sound (e.g., liquid flowing, pump operation, electromechanical components, housing vibrations, machine generated alarms, etc.) has a unique signature that can be monitored to drive a defined set of patient, clinician, and medical device manufacturer interventions. Each sound contains a unique acoustic fingerprint or signature that can be classified based upon learned therapy events, which are representative of normal and abnormal conditions, to drive specific interventions in an attempt to remedy identified issues.

In an aspect, a method of monitoring a medical treatment device includes detecting a sound of the medical treatment device with a detection device, determining whether the sound is an irregular sound, and deploying an intervention upon determining that the sound is the irregular sound.

In some embodiments, the method includes deploying the intervention comprises displaying a notification.

In some embodiments, the notification is a push notification on a smartphone.

In some embodiments, deploying the intervention comprises initiating an audio prompt on a device associated with a patient of the medical treatment device.

In some embodiments, deploying the intervention comprises initiating a phone call to a phone associated with a patient of the medical treatment device.

In some embodiments, deploying the intervention comprises initiating an audio prompt on a device associated with a patient and/or clinician of the medical treatment device to reboot the medical treatment device.

In some embodiments, deploying the intervention comprises initiating the audio prompt on the device associated with the patient and/or clinician to reboot the medical treatment device after confirming that the medical treatment device is in a pretreatment phase.

In some embodiments, the irregular sound is associated with a pump of the medical treatment device.

In some embodiments, determining that the sound is the irregular sound comprises comparing the sound to sound samples stored in a database.

In some embodiments, the sound samples are uploaded to the database and identified through machine learning.

In some embodiments, the irregular sound is indicative of a malfunction of the medical treatment device.

In some embodiments, the irregular sound is indicative of a venous disconnect.

In some embodiments, the irregular sound is indicative of a pump malfunction.

In some embodiments, the medical treatment device is a hemodialysis machine.

In some embodiments, the medical treatment device is a peritoneal dialysis machine.

In an aspect, a medical treatment system includes a medical treatment device, a detection device configured to detect a sound of the medical treatment device, and a processor configured to determine whether the sound is an irregular sound and deploy an intervention upon determining that the sound is the irregular sound.

In some embodiments, the intervention comprises initiating an audio prompt on a device associated with a patient of the medical treatment device to reboot the medical treatment device.

In some embodiments, the detection device includes a microphone.

In some embodiments, the processor is configured to determine whether the sound is an irregular sound by comparing the sound to a database of sounds.

In some embodiments, the sound is indicative of a malfunction of the medical treatment device.

In some embodiments, the sound is indicative of a venous disconnect.

In some embodiments, the sound is indicative of a pump malfunction.

In some embodiments, the sound is a rattling of a housing of the medical treatment device.

3
4

DETAILED DESCRIPTION

This disclosure relates generally to methods for detecting a sound signature (e.g., a sound of liquid flowing, a pump whirring, a housing rattling, electro-mechanical components, etc.) and deploying an intervention (e.g., instructing a patient to run a diagnostic, sending an alert to a medical provider staff member, prompting an incoming telephone call, sending an app notification, etc.) in response to detecting the sound signature. In some cases, a medical fluid pumping system (e.g., a dialysis system, a peritoneal dialysis system, a hemofiltration system, etc.) includes a detection device (e.g., a microphone, smart home devices, smartphones, etc.) actively listening for a sound signature. The detection device actively listens for sound signatures throughout the treatment. In response to detecting a sound signature, the detection device communicates with a server or with the medical fluid pumping system to automate a real-time intervention or trigger support (e.g., notify a clinician, notify a technical support member, run a diagnostic, etc.).

Figure 1:
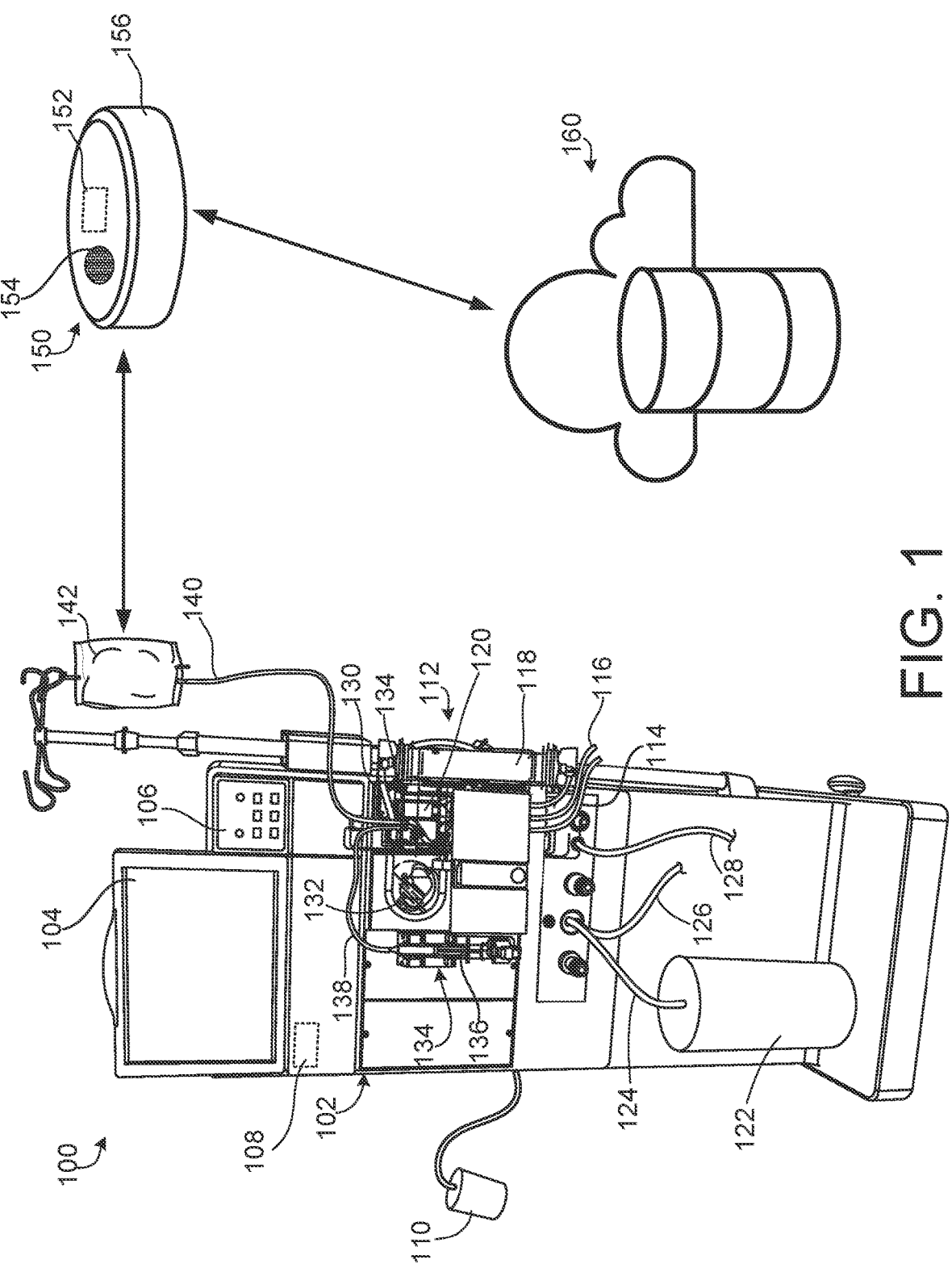
FIG. 1 is a schematic illustration of a hemodialysis system including a hemodialysis machine in communication with a server and a detection device.

Referring to FIG. 1, a hemodialysis system 100 includes a hemodialysis machine 102. The hemodialysis machine 102 includes a touch screen 104 and a control panel 106. The touch screen 104 and the control panel 106 allow the operator to input various information to the hemodialysis machine 102 and to otherwise control the hemodialysis machine 102. In addition, the touch screen 104 serves as a display to convey information to the operator of the hemodialysis system 100.

The hemodialysis machine 102 includes a processor 108 that resides inside the machine that is connected to the touch screen 104 and the control panel 106. The processor 108 is configured to receive data that is input via the touch screen 104 and the control panel 106 and control the hemodialysis machine 102 based on the received data. For example, the processor 108 can adjust the operating parameters of the hemodialysis machine 102.

The hemodialysis machine 102 also includes a Blood Pressure Monitor (BPM) 110 for monitoring a blood pressure of a patient. The BPM 110 may be an automated, non-invasive blood pressure monitor that operates on the principle of oscillometry, such as a blood pressure cuff or sleeve. The BPM 110 may measure systolic blood pressure, diastolic blood pressure, mean arterial pressure (MAP), and information related to the pulse of the patient. While the BPM 110 shown in FIG. 1 is connected to the hemodialysis machine 102 by a wire, in some implementations, the BPM 110 is wirelessly connected to the hemodialysis machine 102 and is able to wirelessly communicate with the hemodialysis machine 102.

A disposable blood component set 112 that forms a blood circuit is connected to the hemodialysis machine 102. During hemodialysis, arterial and venous patient lines 114, 116 of the blood component set 112 are connected to a patient and blood is circulated through various blood lines and components, including a dialyzer 118, of the blood component set 112. At the same time, dialysate is circulated through a dialysate circuit formed by the dialyzer 118 and various other dialysate components and dialysate lines connected to the hemodialysis machine 102. Many of these dialysate components and dialysate lines are located inside the housing of the hemodialysis machine 102, and are thus not visible in FIG. 1. The dialysate passes through the dialyzer 118 along with the blood. The blood and dialysate passing through the dialyzer 118 are separated from one another by a semi-permeable structure (e.g., a semi-permeable membrane and/or semi-permeable microtubes) of the dialyzer 118. As a result of this arrangement, toxins are removed from the patient's blood and collected in the dialysate. The filtered blood exiting the dialyzer 118 is returned to the patient. The dialysate that exits the dialyzer 118 includes toxins removed from the blood and is commonly referred to as "spent dialysate." The spent dialysate is routed from the dialyzer 118 to a drain.

One of the components of the blood component set 112 is an air release device 120. The air release device 120 includes a vent assembly that allows air to pass therethrough while inhibiting (e.g., preventing) liquid from passing therethrough. As a result, if blood passing through the blood circuit during treatment contains air, the air will be vented to atmosphere as the blood passes through the air release device 120.

A dialysate container 122 is connected to the hemodialysis machine 102 via a dialysate supply line 124. A drain line 126 and an ultrafiltration line 128 also extend from the hemodialysis machine 102. The drain line 126 and ultrafiltration line 128 can be connected to a drain. The dialysate supply line 124, the drain line 126, and the ultrafiltration line 128 are fluidly connected to the various dialysate components and dialysate lines inside the housing of the hemodialysis machine 102 that form part of the dialysate circuit. During hemodialysis, the dialysate supply line 124 carries fresh dialysate from the dialysate container 122 to the portion of the dialysate circuit located inside the hemodialysis machine 102. As noted above, the fresh dialysate is circulated through various dialysate lines and dialysate components, including the dialyzer 118, that form the dialysate circuit. As the dialysate passes through the dialyzer 118, it collects toxins from the patient's blood. The resulting spent dialysate is carried from the dialysate circuit to a drain via the drain line 126. When ultrafiltration is performed during treatment, a combination of the spent dialysate and excess fluid drawn from the patient is carried to the drain via the ultrafiltration line 128.

The blood component set 112 is secured to a module 130 on the front of the hemodialysis machine 102. The module 130 includes a blood pump 132 capable of driving blood through the blood circuit. The module 130 also includes various other instruments capable of monitoring the blood flowing through the blood circuit. The module 130 includes a door that when closed, as shown in FIG. 1, cooperates with the front face of the module 130 to form a compartment sized and shaped to receive the blood component set 112. In the closed position, the door presses certain blood components of the blood component set 112 against corresponding instruments exposed on the front face of the module 130. This arrangement facilitates control of the flow of blood through the blood circuit and monitoring of the blood flowing through the blood circuit.

A drug pump 134 also extends from the front of the hemodialysis machine 102. The drug pump 134 is a syringe pump that includes a clamping mechanism configured to retain a syringe 136 of the blood component set 112. The drug pump 134 also includes a stepper motor configured to move a plunger of the syringe 136 along an axis of the syringe 136. A shaft of the stepper motor is secured to the plunger in a manner such that when the stepper motor is operated in a first direction, the shaft forces the plunger into the syringe, and when operated in a second direction, the shaft pulls the plunger out of the syringe 136. The drug pump 134 can thus be used to inject a liquid drug (e.g., heparin) from the syringe 136 into the blood circuit via the drug delivery line 138 during use, or to draw liquid from the blood circuit into the syringe 136 via the drug delivery line 138 during use.

The dialysate circuit is formed by multiple dialysate components and dialysate lines positioned inside the housing of the hemodialysis machine 102 as well as the dialyzer 118, a dialyzer inlet line, and a dialyzer outlet line that are positioned outside of the housing of the hemodialysis machine 102. The dialyzer inlet line includes a connector adapted to connect to one end region of the dialyzer 118, and the dialyzer outlet line includes a connector adapted to connect to another end region of the dialyzer 118.

In addition to the blood lines forming the main blood circuit described above, a saline delivery line 140 and the drug delivery line 138 are connected to the blood circuit for introducing saline and drugs (e.g., heparin) into the blood circuit. The saline delivery line 138 is connected to a saline bag 142. The drug delivery line 138 is connected to the syringe 136 that contains a drug.

The hemodialysis system 100 also includes a detection device 150 which includes a processor 152, a microphone 154, and a speaker 156. In this example, the detection device 150 is a smart home device, which can detect sounds and process commands. Some examples of smart home devices include Google Nest, Amazon Echo, and Apple HomePod, but any of various other smart home devices may be used. The processor 152 provides advanced sound processing capabilities so that the detection device 150 can actively listen for unique sound signatures before, during, or after use of the hemodialysis machine 102. Actively listening can, for example, include processing sounds detected by the microphone 154 to determine whether the detected sound matches a predetermined sound signature.

The detection device 150 is configured to communicate with a server 160, e.g., via an internet connection. The server 160 can be accessible by many medical facilities of various types. In some implementations, the server 160 is accessible by most or all medical facilities affiliated with a particular dialysis service provider. In certain implementations, the server 160 is accessible by most or all medical facilities in a particular country or in multiple countries. The server 160 is populated with data that is accessible by the detection device 150, as explained in more detail below. The detection device 150 is configured to receive data from the server 160 and actively listen to the hemodialysis machine 102 based on the received data. For example, the server 160 can provide sound signatures that activate the detection device 150 and deploy an intervention. The detection device 150 is also configured to upload data to the server 160. As will be discussed below, the detection device 150 can upload sounds that occur during treatment to the server 160. The server 160 can use the uploaded sounds to determine regular and irregular sounds.

Figure 2B:
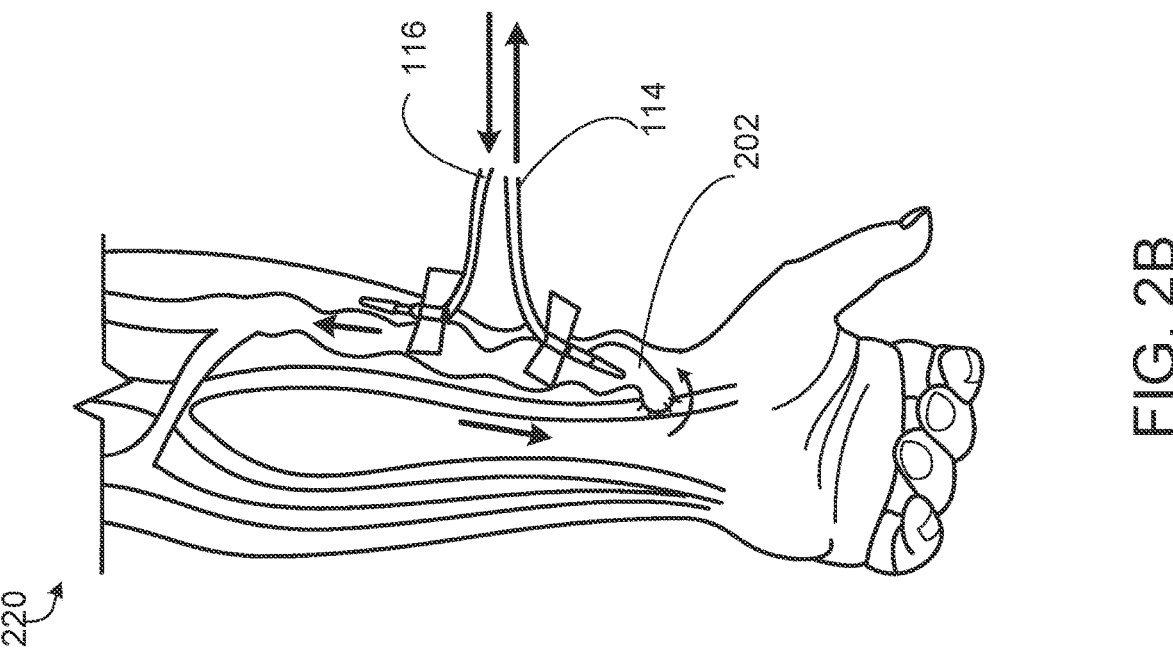
FIGS. 2A and 2B are illustrations of a proper connection of arterial and venous patient lines to a patient and a venous disconnect, respectively, occurring during a treatment carried out by the hemodialysis system of FIG. 1.
Figure 2A:
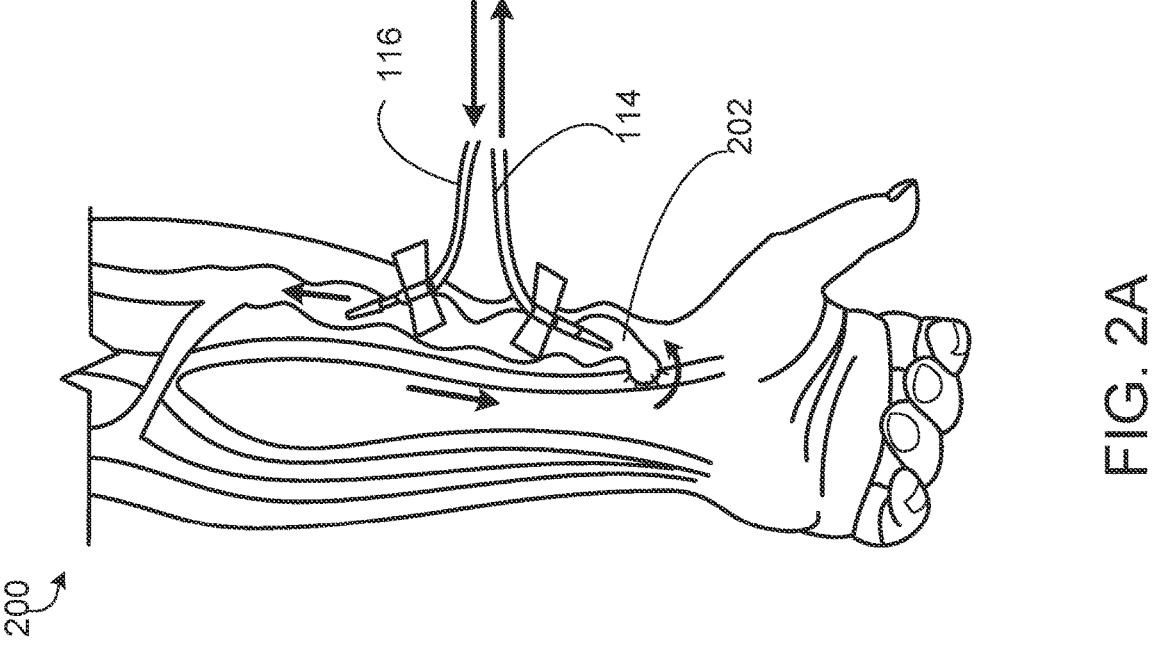

FIGS. 2A and 2B respectively illustrate a proper connection 200 of the arterial and venous patient lines 114, 116 to a hemodialysis patient and a venous disconnect 220 in which the venous patient line 116 has become disconnected or partially disconnected from the patient. In the illustrated example of a proper connection 200 to a patient shown in FIG. 2A, the arterial and venous patient lines 114, 116 connect to an arteriovenous fistula 202, which includes one or more arteries directly connected to one or more veins or venous spaces. Arteriovenous fistulas or grafts can be created for dialysis to provide increased blood flow. As illustrated by the proper connection 200, the arterial and venous patient lines 114, 116 are properly positioned and sufficiently inserted into the arteriovenous fistula 202.

In contrast, in the illustrated venous disconnect 220 shown in FIG. 2B, the venous patient line 116 is improperly positioned and is thus not sufficiently inserted into the arteriovenous fistula 202. A venous disconnect 220 can cause a patient to lose a significant amount of blood within a matter of minutes. Therefore, it can be advantageous to identify the venous disconnect as soon as possible.

A venous disconnect can create unique sounds that are normally not present during hemodialysis treatment. For example, a patient or clinician does not typically hear the sound of blood flowing during a normal hemodialysis treatment. However, in the event of a venous disconnect or leakage in fluid lines (e.g., the arterial and venous patient lines 114, 116, the blood component set 112) of the hemodialysis machine, sounds such as the swishing of blood, liquid flowing, or air flowing can emerge. These irregular sounds can be recognized by a detection device, which can deploy an intervention accordingly, as described below.

The server 160 contains a list of predetermined sound signatures and interventions. A sound signature is one or more discrete data elements (intensity values, centroid values, spread values, skewness values, kurtosis values, decrease values, Mel-frequency cepstral coefficients, etc.) which represent a unique sound. Each predetermined sound signature can be paired with an intervention, and the server 160 can provide the detection device 150 with a list of sound signatures and their respective interventions. One of the predetermined sound signatures can be discrete data elements which are representative of blood swishing.

The detection device 150 actively listens to a hemodialysis treatment. When a venous disconnect occurs during treatment, it can produce a sound of blood swishing (e.g., in the patient lines). The detection device processes the detected sound of blood swishing into a sound signature (e.g., one or more discrete data elements). The processor of the detection device then compares the detected sound signature to a list of predetermined sound signatures provided by the server 160. In this case, the detected sound signature of blood swishing matches a predetermined sound signature provided by the server 160.

When the detection device 150 detects a sound signature that matches a predetermined sound signature provided by the server 160, the detection device 150 can deploy an intervention. In the example of a venous disconnect, the detection device 150 can initiate an audio prompt to the patient, care-partner, or clinician using the speaker 154. For example, the audio prompt can include instructions to a clinician to occlude blood flow or to seek emergency medical attention. The audio prompt can bring immediate attention to the venous disconnect, which otherwise could go unnoticed for a period of time.

Using a smart home device as a detection device 150 comes with several advantages. For example, certain implementations are advantageous because safety can be increased without modification of the dialysis machine. A patient can use an off the shelf device to improve his or her dialysis experience. A patient also does not need to get a new dialysis machine to benefit from the present methods and systems. Additionally, many smart home devices can be programmed to detect a variety of sound signatures and include processors which can initiate interventions. Using a smartphone as a detection device 150 provides similar advantages.

Figure 3:
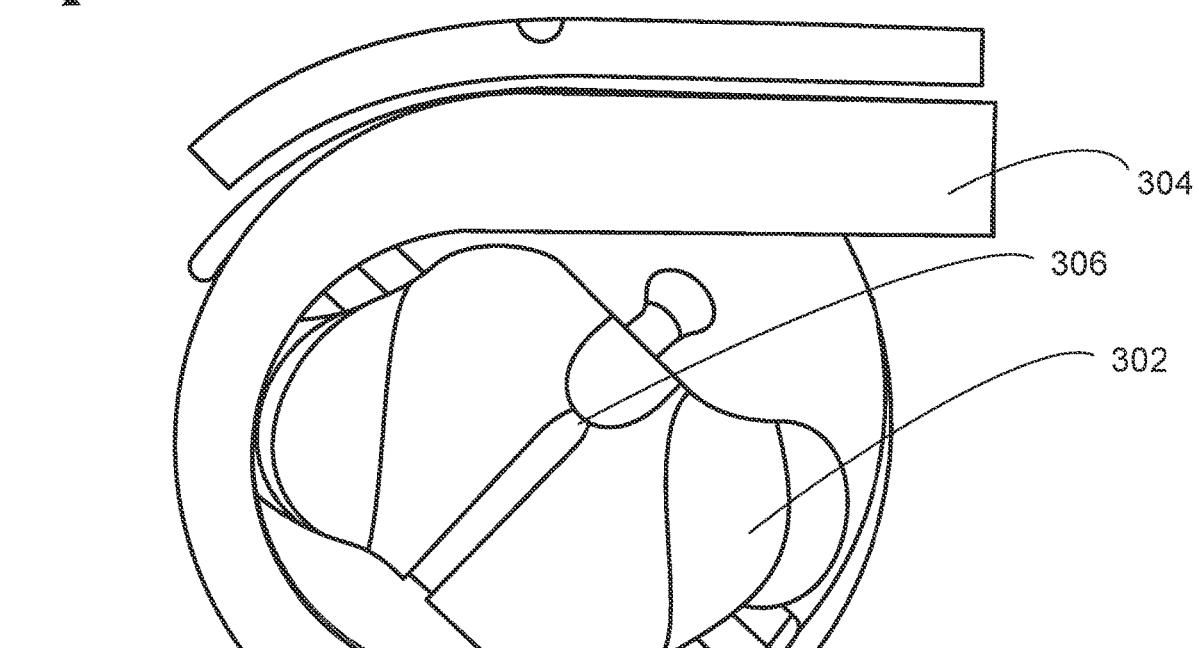
FIG. 3 is an illustration of a blood pump of the hemodialysis machine of FIG. 1.

Other sounds can also cause the detection device 150 to initiate interventions. For example, irregular sounds made by the blood pump 132 may be an indication of a malfunction. FIG. 3 is an enlarged view of the blood pump 132 of the hemodialysis machine 102. The blood pump 132 is a peristaltic pump that includes rollers 302 which compress the fluid line 304 as the blood pump 132 rotates about the center 306 of the blood pump. The pump 132 generally rotates at a constant speed. During normal operation, the pump 132 does not make loud noises, such as banging or whirring noises. However, during a mechanical malfunction or failure, the rollers 302 may bang against the walls of the pump 132, or the pump 132 may make a whirring sound that is louder than a pump operating normally. Additionally, the pump 132 will typically make a constant or continuous noise and will typically not make sounds in an irregular pattern when operating normally. Banging, whirring, or other irregular noises can be indicative of a pump malfunction.

The detection device 150 can actively listen to a hemodialysis treatment, as described above. When the blood pump 132 is malfunctioning, it can produce a whirring sound. The detection device processes the detected whirring sound into a sound signature (e.g., one or more discrete data elements). The processor of the detection device then compares the detected sound signature to the predetermined sound signatures provided by the server 160. In this case, the server 160 provides a predetermined sound signature that is representative of the pump whirring.

When the detection device 150 detects a sound signature that matches a predetermined sound signature provided by the server 160 that is associated with a malfunction of the blood pump 132, the detection device 150 can deploy an intervention. In the example of a pump whirring, the detection device 150 can initiate an audio prompt to the patient, a care-partner, or a clinician using the speaker 154 to request more information from the patient or clinician to identify whether the system is in pretreatment (e.g., setting up for treatment), mid treatment, or post treatment. If the system is in pretreatment or post treatment, the detection device 150 can initiate an audio prompt to the patient, a care-partner, or a clinician to reboot the system or to run a diagnostic. If the system is mid treatment, the detection device 150 can initiate an audio prompt to the patient, a care-partner, or a clinician to run a diagnostic after treatment is finished. If the sound signature doesn't indicate a critical or catastrophic failure, the patient, care-partner, or clinician can be prompted to complete the treatment. This can be advantageous since stopping the treatment early can cause the patient to retain extra fluid, which can cause swelling, and can cause the patient to retain more waste products that should be eliminated. Stopping the treatment early can be avoided by determining the phase of the treatment and the nature of the malfunction before providing instructions to the patient, care-partner, or clinician.

Figure 4:
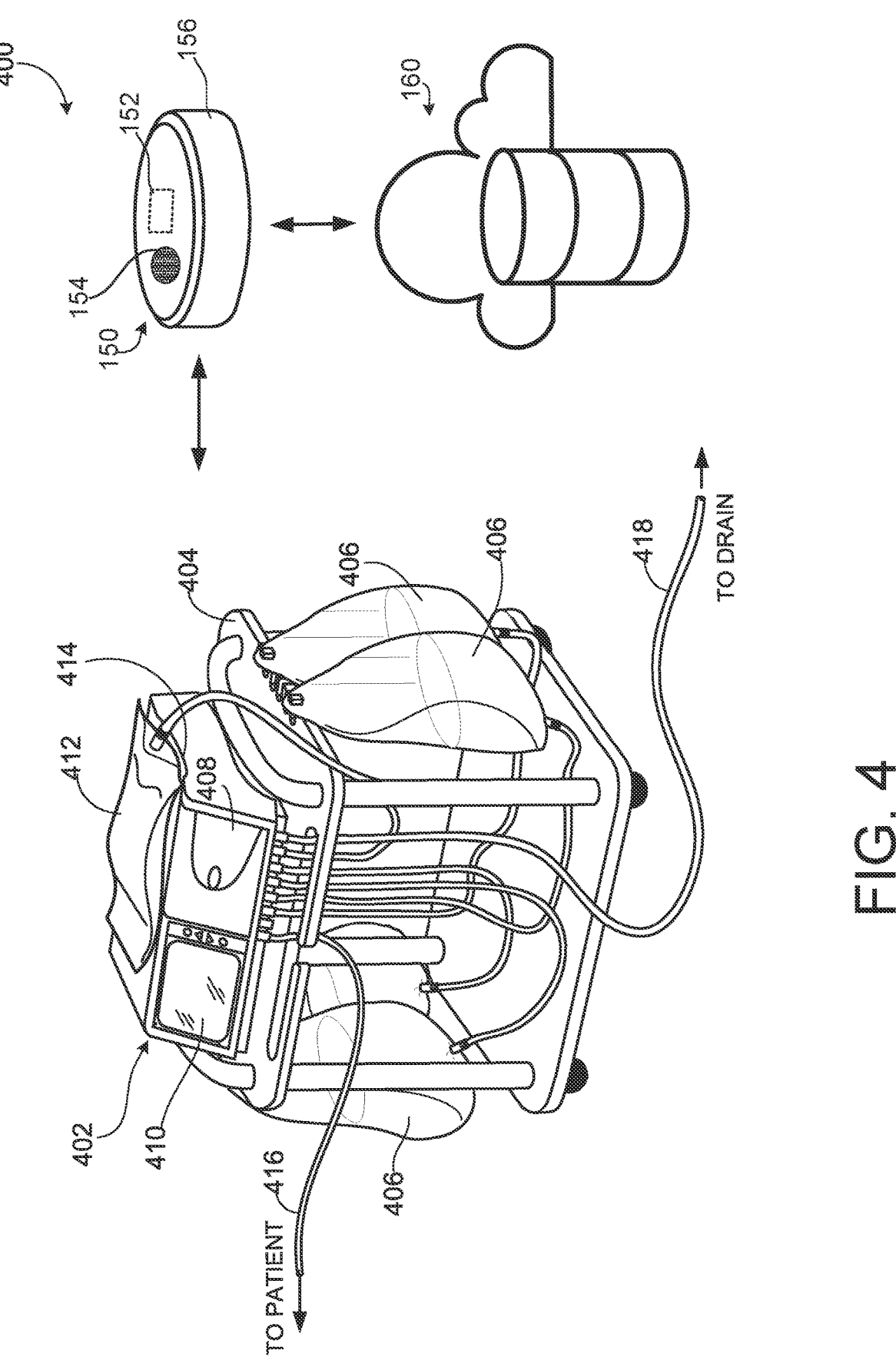
FIG. 4 is a schematic illustration of a peritoneal dialysis ("PD") system including a PD cycler in communication with a server and a detection device.

The detection device 150 and the server 160 can also be used with other types of medical equipment. One example of another type of medical equipment with which the detection device 150 and the server 160 can be used, as shown in FIG. 4, is a PD system 400 that includes a PD cycler 402, a cart 404, four PD solution bags 406 and their associated fluid lines, and a disposable PD cassette 500 (positioned behind a door 408 of the PD cycler 402 in FIG. 4 and shown in FIG. 5A) to direct fluids during treatment. The PD cycler 402 includes a touch screen 410, forming the control panel for the patient interface operated by the patient. The cycler 402 is seated on top of the cart 404, which is designed to accommodate the PD solution bags and associated fluid lines.

The PD solution bags 406 are suspended from fingers on the sides of the cart 404 as shown. A heater bag 412 is shown lying in a shallow concave depression forming a heater tray 414, which is sized and shaped to accommodate a typical five liter bag of PD solution. The heater tray 414 has a plurality of heating coils embedded below the surface. A temperature sensor is positioned in the surface of the heater tray 414 to track the temperature of the solution in the heater bag for a thermostatic control circuit that turns the heating coils on and off as needed to maintain the PD solution at the desired temperature. The cassette is inserted into a cassette compartment formed between the hinged door 408 and a cassette interface of the PD cycler 402 when the door 408 is closed and securely latched. Because the dialysis solution bags 406, the heater bag 412, the patient line 416, and the drain line 418 are connected to the cassette, dialysis solution is allowed to flow into and out of the cassette during use.

Typical PD machines utilize six fluid-processing sequences: flush, prime, drain, fill, pause, and dwell. The purpose of the flush sequence is to remove air from all the lines (except the patient line 416) and from the cassette. This is accomplished by pumping dialysate solution through the lines to be flushed. The prime sequence removes air from the patient line 416 by pumping dialysate solution from the heater bag through the patient line 416.

During PD treatment, the patient line 416 is connected to a patient's abdomen via a catheter. The PD treatment typically begins by emptying the patient of spent dialysis solution that remains in the patient's abdomen from the previous treatment. To do this, the PD cycler is activated to draw the spent dialysis solution into the cassette from the patient. The spent dialysis solution is then pumped from the cassette to the drain line 418.

After draining the spent dialysis solution from the patient, heated dialysis solution is transferred from the heater bag 412 to the patient. To do this, the PD cycler is activated to cause the warmed dialysis solution to be drawn into the cassette from the heater bag 412. The warmed dialysis solution is then pumped from the cassette to the patient via the patient line 416.

Once the dialysis solution has been pumped from the heater bag 412 to the patient, the dialysis solution is allowed to dwell within the patient for a period of time. During this dwell period, toxins cross the peritoneum of the patient into the dialysis solution from the patient's blood. As the dialysis solution dwells within the patient, the PD cycler 402 prepares a fresh dialysate to deliver to the patient in a subsequent cycle. In particular, the PD cycler 402 pumps fresh dialysis solution from one of the full dialysis solution bags 406 into the heater bag 412 for heating. To do this, the pump of the PD cycler 402 is activated to draw the dialysis solution into the cassette from the selected dialysis solution bag 406. The dialysis solution is then pumped from the cassette to the heater bag 412.

After the dialysis solution has dwelled within the patient for the desired period of time, the spent dialysis solution is pumped from the patient to the drain line 418. The heated dialysis solution is then pumped from the heater bag 412 to the patient where it dwells for a desired period of time. These steps are repeated with the dialysis solution from two of the three remaining dialysis solution bags 406. The dialysis solution from the last dialysis solution bag 406 is typically delivered to the patient and left in the patient until the subsequent PD treatment. The pause sequence allows the patient to disconnect from the machine once the patient has been filled with dialysate solution.

In the example illustrated in FIG. 4, the detection device 150 can actively listen for sound signatures before, during, or after use of the PD cycler 402. The detection device 150 also communicates with the server 160. The detection device 150 is configured to receive data from the server 160 and actively listen to the PD cycler 402 based on the received data. For example, the server 160 can provide sound signatures that activate the detection device 150 and deploy an intervention. The detection device 150 is also configured to upload data to the server 160. For example, the detection device 150 can upload sounds to the server 160. As will be discussed below, the detection device 150 can upload sounds that occur during treatment to the server, and the server can use the uploaded sounds to determine regular and irregular sounds.

Figure 5A:
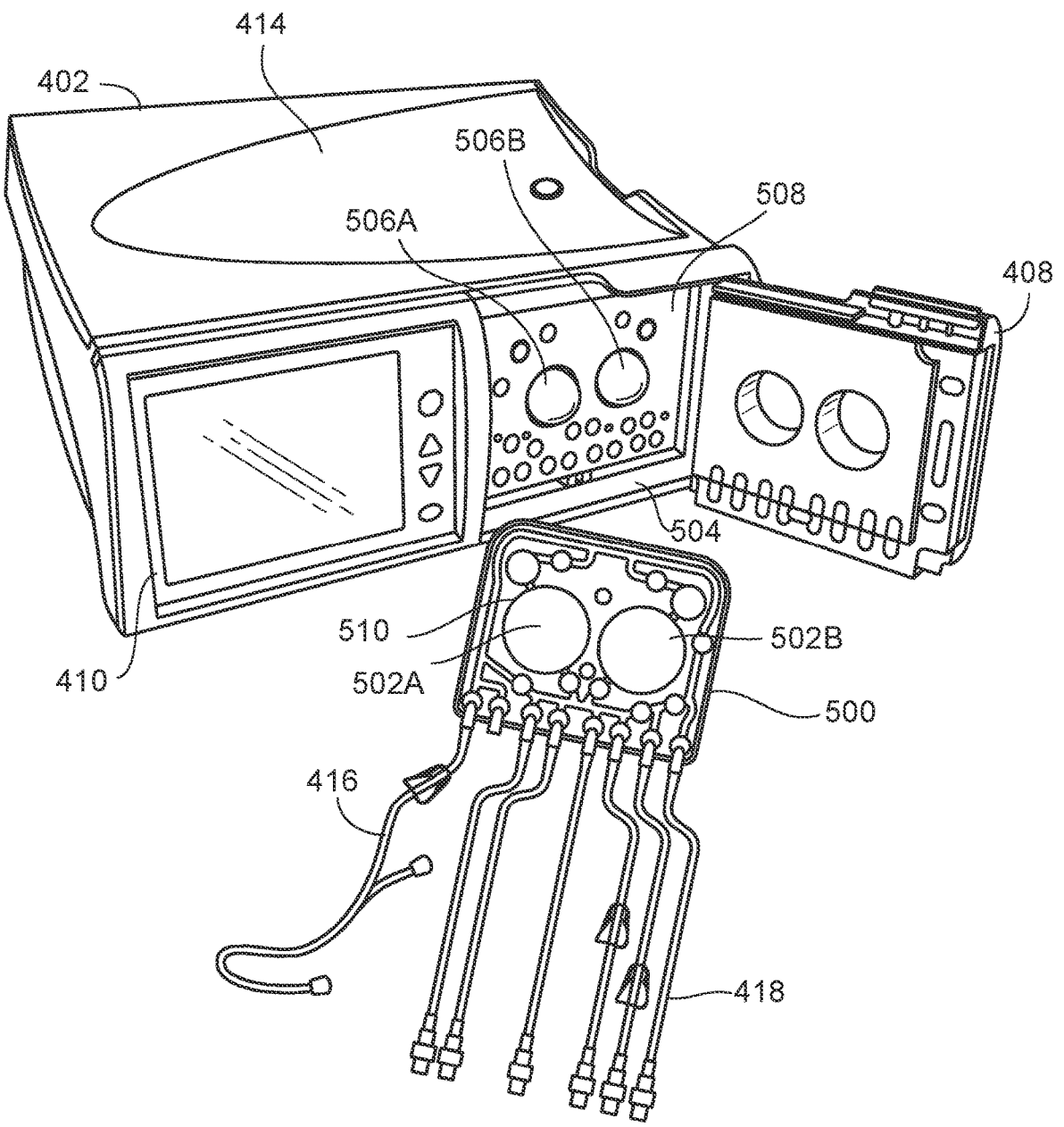
FIG. 5A is a perspective view of the PD cycler and a PD cassette of the PD system of FIG. 4. A door of the PD cycler is in the open position to show the inner surfaces of the PD cycler that interface with the PD cassette during use.

FIG. 5A is a partially exploded view of the PD cycler 402 and the PD cassette 500. The cassette 500 includes fluid pathways to allow fluid to flow through the cassette 500. The fluid pathways in the cassette 500 lead from pumping chambers 502A, 502B to connectors positioned along the bottom edge of the cassette 500. The connectors are configured to receive fittings on the ends of the PD solution bag lines, the heater bag line, the patient line 416, and the drain line 418. These fittings can, for example, be double male fittings. One end of the fitting can be inserted into and bonded to its respective line and the other end can be inserted into and bonded to its associated connector. By permitting the PD solution bag lines, the heater bag line, the patient line 416, and the drain line 418 to be connected to the cassette, the connectors allow PD solution to flow into and out of the cassette 500 during use.

When the door 408 is in the open position, as shown in FIG. 5A, the cassette 500 can be loaded onto the cassette interface 504 by positioning the top portion of the cassette 500 under locating pins and pushing the bottom portion of the cassette 500 toward the cassette interface 504. The cassette 500 is dimensioned to remain securely positioned between the locating pins and a lower ledge extending from the cassette interface 504 to allow the door 408 to be closed over the cassette 500. The locating pins help to ensure that the pump chambers 502A, 502B of the cassette 500 are aligned with piston heads 506A, 506B of piston pumps of the PD cycler 402 when the cassette 500 is positioned in the cassette enclosure 508 between the closed door 408 and the cassette interface 504.

Figures 5B, 5C, 5D:
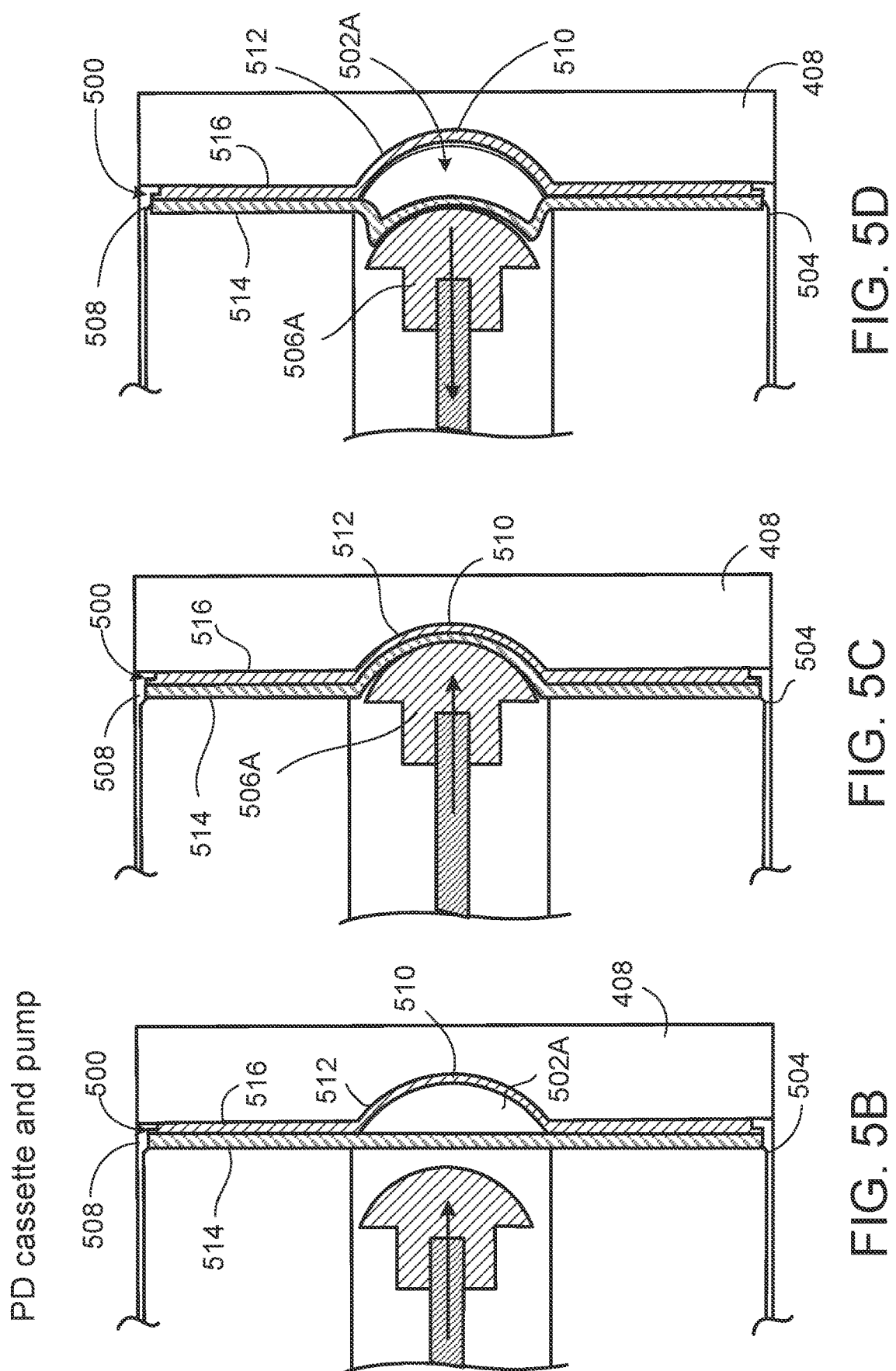
FIGS. 5B-D are diagrammatic cross-sectional views of the PD cassette in a cassette compartment of the PD cycler of the PD system of FIG. 4, during different phases of operation.

Referring to FIG. 5B, with the cassette 500 positioned adjacent to the cassette interface 504, the door 408 is closed over the cassette 500 such that the cassette 500 is substantially contained within the cassette enclosure 508 between the door 408 and the cassette interface 504. As shown, hemispherical projections 510 of the cassette 500 fit within the recesses 512 in the door 408. The PD cycler utilizes a vacuum system to move the portions of the membrane 514 overlying the pump chambers 502A, 502B. Therefore, a substantially airtight seal between the door 408 and the cassette interface 504 is typically required.

As shown in FIG. 5C, with the cassette 500 secured within the enclosure 508, the piston heads 506A, 506B are moved outward (e.g., to a substantially fully extended position) to contact the regions of the cassette membrane 514. In the fully extended position, the inner surface of the membrane 514 comes into contact or near contact with the inner surface of the hemispherical projections 510 of the rigid base 516 of the cassette 500. The vacuum system secures the piston heads 506A, 506B to the membrane 514.

With the piston heads 506A, 506B secured to the membrane 514, PD solution can be drawn into the pump chambers 502A, 502B of the cassette 500 by retracting the membrane 514 along with the piston heads 506A, 506B to increase the volume of the pump chambers 502A, 502B, as shown in FIG. 5D. The fluid can then be forced out of the pump chambers 502A, 502B by again returning the piston heads 506A, 506B to the position shown in FIG. 5C, causing the membrane 514 to move toward the rigid base 516 and thus decreasing the volume of the pump chambers 502A, 502B. While forcing PD solution into and out of the pump chambers 502A, 502B, certain inflatable members of the PD cycler 402 can be selectively inflated to direct the pumped PD solution along desired pathways in the cassette 500.

During normal operation, the pistons will not generally make irregular noises, such as banging, and will typically have a consistent rhythm. Banging, irregular rhythm, or other irregular noises can be indicative of a malfunction. The detection device 150 can actively listen for, e.g., sounds generated by operation of the piston pumps of the PD cycler 402.

The detection device 150 can actively listen to a PD treatment, as described above. When the piston pumps are malfunctioning, they can produce an irregular rhythm. The detection device processes the sound of the detected irregular sound and converts the sound into one or more discrete data elements (i.e., a sound signature). The processor of the detection device 150 then compares the detected sound signature to the predetermined sound signatures provided by the server 160. In this case, for example, the server 160 can provide a predetermined sound signature that is representative of banging of the pistons or an irregular rhythm of the pistons.

When the detection device 150 detects a sound signature that matches a predetermined sound signature provided by the server 160, the detection device 150 can deploy an intervention. In the example of banging of the pistons or an irregular rhythm of the pistons, the detection device 150 can initiate an audio prompt to the patient, a care-partner, or a clinician using the speaker 154 to request more information from the patient or clinician to identify whether the system is in pretreatment (e.g., setting up for treatment), mid treatment, or post treatment. If the system is in pretreatment or post treatment, the detection device 150 can initiate an audio prompt to the patient, a care-partner, or a clinician to reboot the system or to run a diagnostic. If the system is mid treatment, the detection device 150 can initiate an audio prompt to the patient, a care-partner, or a clinician to run a diagnostic after treatment is finished. If the sound signature doesn't indicate a critical or catastrophic failure, the patient, care-partner, or clinician can be prompted to complete the treatment.

In some embodiments, the detection device can communicate directly with the hemodialysis machine. For example, one or more hardwire connections (e.g., serial cable, parallel cable, etc.) may be implemented. Wireless techniques such as infrared (IR), radio frequency (RF), Bluetooth, wireless Ethernet, or other electromagnetic linking techniques, may also be used. One or more protocols, transmission standards, and data formats may also be used for passing information between the detection device 150 and the hemodialysis machine 102.

Figure 6:
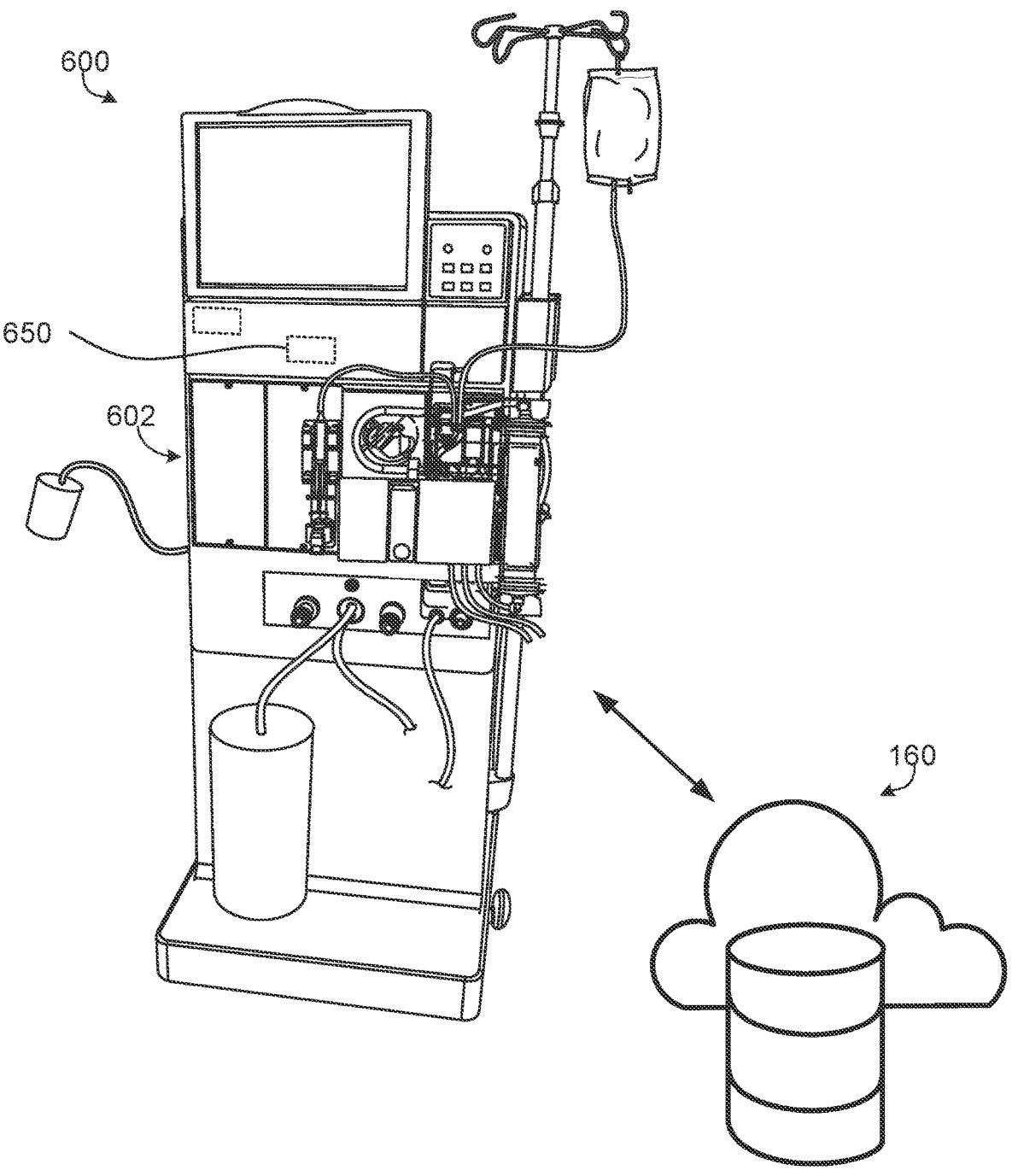
FIG. 6 is a schematic illustration of a hemodialysis system including a hemodialysis machine with an integrated detection device, where the hemodialysis machine is in communication with a server.

In some implementations, the detection device may not be a separate device and is instead a part of the medical fluid pumping machine. For example, FIG. 6 illustrates a system 600 including a detection device 650 integral with a hemodialysis machine 602. Other than the integration of the detection device 650 with the hemodialysis machine 602, the components of the hemodialysis machine 602 can be the same as the components of the hemodialysis machine 102. Integrating the detection device 650 with the hemodialysis machine 602 can be useful because the detection device can communicate directly with the hemodialysis machine. For example, the server 160 can provide sound signatures that activate the detection device 650 and deploy an intervention. The detection device 650 is also configured to upload data to the server 160. For example, the detection device 650 can upload sound signatures to the server 160, as will be discussed below.

The detection device 650 can actively listen to a hemodialysis treatment, as described above. When a pump of the hemodialysis machine 602 is malfunctioning, it can produce a whirring sound. The detection device 650 processes the detected whirring sound into a sound signature (e.g., one or more discrete data elements). The processor of the detection device then compares the detected sound signature to the predetermined sound signatures provided by the server 160. In this case, the server 160 provides a predetermined sound signature that is representative of the pump whirring.

When the detection device 650 detects a sound signature that matches a predetermined sound signature provided by the server 160, the detection device 650 can deploy an intervention. In the example of a pump whirring, the detection device 650 can automatically detect whether the system is in pretreatment (e.g., setting up for treatment), mid treatment, or post treatment. If the system is in pretreatment or post treatment, the detection device 650 can cause the hemodialysis machine to reboot the system or to run a diagnostic. If the system is mid treatment, the detection device 650 can cause the hemodialysis machine to run a diagnostic after the treatment is finished. Because the detection device 650 can communicate directly with the hemodialysis machine, the detection device no longer requires the patient to reboot the system or run a diagnostic manually.

In some embodiments, a processor of the dialysis machine deploys the intervention. For example, upon the detection device 650 detecting a sound signature that matches with a predetermined sound signature provided by the user, the processor of the dialysis machine can reboot the system or run a diagnostic.

Figure 7:
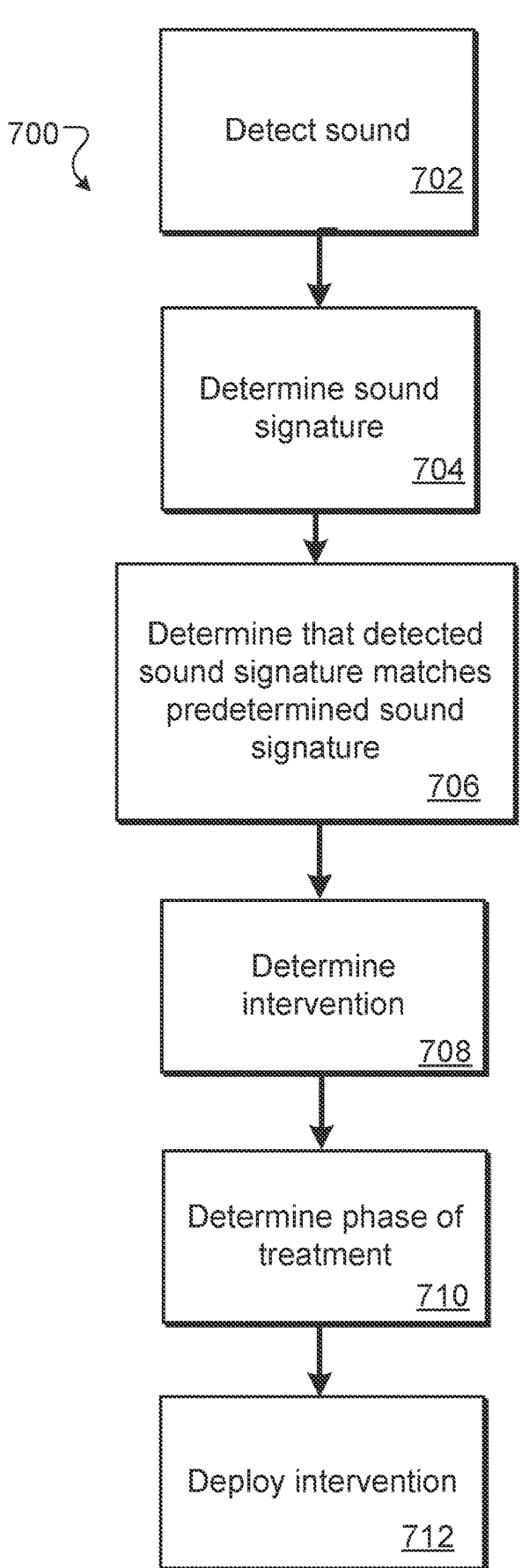
FIG. 7 is a method of deploying an intervention in response to detecting sound.

FIG. 7 illustrates a flowchart of a method of detecting sound and deploying an intervention. The method begins with detecting sound. For example, a detection device can detect sound (702) as described above. The sound is processed to determine a sound signature (704). For example, the sound can be processed into one or more discrete data elements that are representative of a sound signature. Next, the detected sound signature determines that the detected sound signature matches a predetermined sound signature (706). For example, the detected sound signature is compared to a list of predetermined sound signatures to determine that the detected sound signature matches a predetermined sound signature be provided by a database or server. An appropriate intervention is determined based on the predetermined sound signature (708). For example, each predetermined sound signature can be linked to an intervention (e.g., through a look-up table). The method can include determining a phase of treatment (e.g., pretreatment, mid treatment, post treatment) (710) after determining that the detected sound signature matches a predetermined sound signature. For example, the method can include initiating an audio prompt to a patient, a care-partner, or a clinician and requesting more information from the patient or clinician to identify whether the system is in pretreatment (e.g., setting up for treatment), mid treatment, or post treatment. After determining a phase of treatment, an intervention is deployed (712). For example, deploying an intervention can include an audio prompt to the patient, a care-partner, or a clinician to reboot the system or to run a diagnostic. In another example, deploying an intervention can include rebooting the system or running a diagnostic.

The server described herein can be updated to include more sound signatures and interventions. For example, because the detection device is actively listening during treatment, the sound signatures that occur during the course of the treatment can be uploaded to the database. The sound can be processed (e.g., echo cancelation, noise reduction, digital processing to suppress unwanted signatures) on the detection device to anonymize sound signatures before uploading the sound signatures to the server. If no errors or alarms occur during the course of the treatment, then the sound signatures of the treatment can be uploaded to the database and stored as 'normal operation' sound signatures. For example, sound signatures of normally operating machines can be uploaded and stored as normal operation sound signatures. If the machine is determined to have malfunctioned during or after the treatment, the sound signatures that occur over the course of the treatment can be uploaded to the database and used to determine new predetermined sound signatures that are indicative of malfunctions.

To identify new predetermined sound signatures, the server can process (e.g., through artificial intelligence or machine learning as described below) sound signatures of the treatment. The server can compare the sound signatures of the malfunctioning treatment to the sound signatures of stored 'normal operation' sound signatures. If a certain sound signature often occurs before a certain type of failure, then the sound signature can be indicative of that type of failure. For example, if a blood pump makes a whirring noise before failing, then the sound signature of the whirring noise can be indicative of a blood pump failure. Once the server identifies a sound signature that is indicative of a certain type of failure, the server can update the list of predetermined sound signatures to include the new sound signature.

One or more machine learning techniques may be employed. For example, supervised learning techniques may be implemented in which training is based on a desired output that is known for an input. Supervised learning can be considered an attempt to map inputs to outputs and then estimate outputs for previously unseen inputs (a newly introduced input). Unsupervised learning techniques may also be employed in which training is provided from known inputs but unknown outputs. Reinforcement learning techniques may also be used in which the system can be considered as learning from consequences of actions taken (e.g., inputs values are known and feedback provides a performance measure). In some arrangements, the implemented technique may employ two or more of these methodologies.

Figure 8:
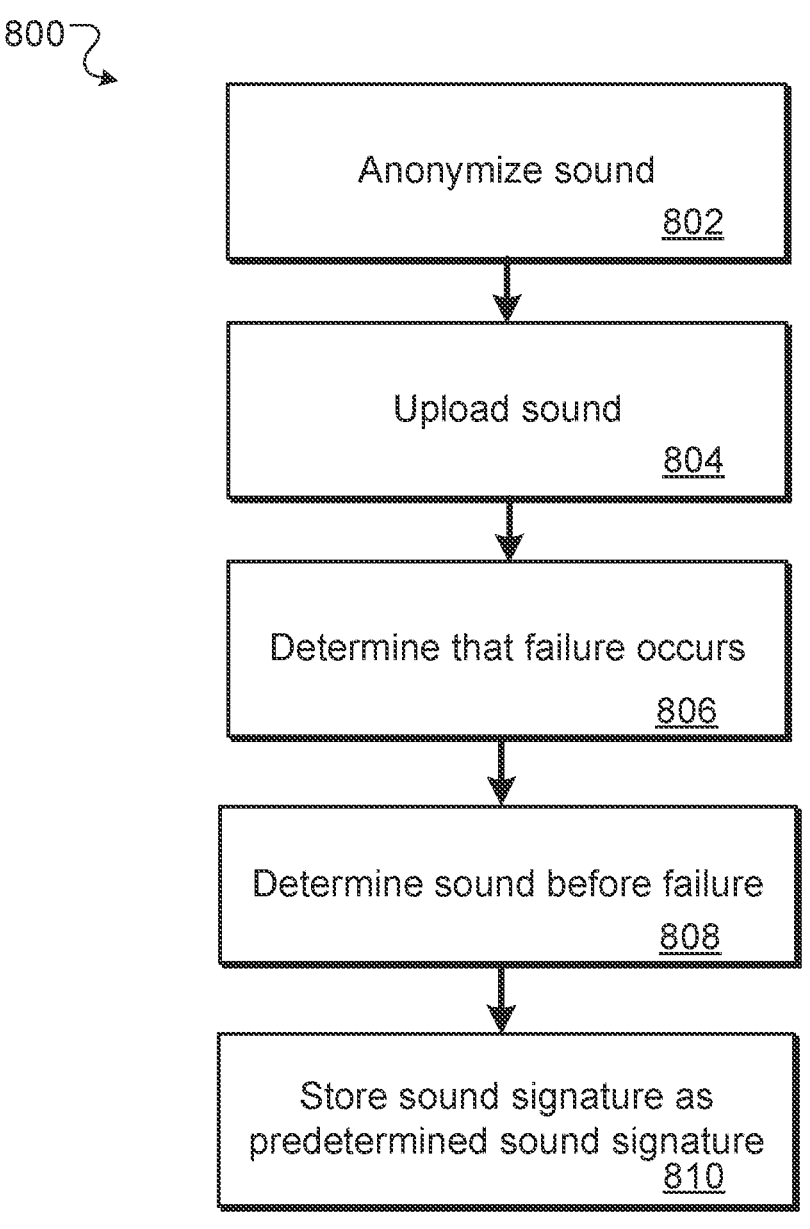
FIG. 8 is a method of storing a sound signature in a database.

FIG. 8 illustrates a flowchart of a method for determining new sound signatures indicative of a failure. First, the sounds detected during treatment are processed to anonymize the sounds and turn the sounds into sound signatures (802). For example, the detection device can process the sounds detected during a treatment, as described above. Then, the sound signatures are received (804). The server determines that a failure or malfunction occurred during the course of the treatment (806). For example, the server can receive confirmation that a failure occurred during the treatment, e.g., at a specific time. The server then analyzes the sound signatures, e.g., at the time that the failure occurred or before the failure occurred, to determine the sound signature that occurs before failure (808). For example, the server can compare the sound signatures of the malfunctioning treatment to the sound signatures of stored 'normal operation' sound signatures. If the sound signature is indicative of a certain type of failure then the sound signature can be stored in the list as a predetermined sound signature (810).

While the detection devices has been described as actively listening for the duration of a treatment, in some embodiments, the detection devices actively listen for only portions of the treatment. For example, the detection devices can actively listen for specific phases of the treatment (e.g., pretreatment, mid treatment, post treatment). In some embodiments, the detection devices sample the sounds throughout the treatment (e.g., the detection devices actively listen for a few seconds, e.g., every 15 seconds).

While specific sounds have been described, other sounds that occur during treatment can be utilized as predetermined sound signatures. For example, rattling or shaking of the machine can be stored as predetermined sound signatures. In another example, machine generated alarms or notifications can be stored as predetermined sound signatures. In another example, irregular sounds of electromechanical components (e.g., fans, servomotors, heaters, etc.) of the machine can be stored as predetermined sound signatures. In another example, power sequences (e.g., powering on or off) of machines can be stored as predetermined sound signatures. The swishing of blood, liquid flowing, or air flowing can also be indicative of leaking fluid lines and can be stored as predetermined sound signatures. For example, dialysate, blood, or substitution fluid may leak from the fluid lines of a dialysis machine that is malfunctioning.

While specific interventions have been described, other interventions can be utilized. One example of an intervention is an audio prompt to the local patient, care-partner, or clinician including instructions to the patient to attempt to triage the issue or call technical support or their nurse from their clinic. Another example of an intervention is an alert or notification sent to a clinical web dashboard for a healthcare provider staff member. Yet another example of an intervention is an alert or notification sent to a medical device manufacturer staff member (e.g., a technical or customer support staff member). Another example of an intervention is a prompt for an incoming communication (e.g., a voice call, video chat, text message) for the patient to communicate with a medical device manufacturer staff member or a clinician. Another example of an intervention is a remote software update to the treatment system. Another example of an intervention is an app notification that is sent to the patient. For example, the patient may have an app (e.g., the Fresenius Health Tracker App) on a smartphone that allows the patient to receive a push notification on a home screen of the smartphone.

While certain types of detection devices have been described, other types of detection devices may be used. Some examples of detection devices are smartphones, smart watches, tablets, laptops, smart home devices, Fresenius Kinexus™ Gateways, smart televisions, etc. Devices that include a microphone and processor and can communicate with a server can be utilized as detection devices as described above.

Although the predetermined sound signatures have been described as being identified by the server (e.g., through machine learning or artificial intelligence), in some embodiments, predetermined sound signatures can be identified and uploaded by a nurse, clinician, medical device manufacturer, or patient. For example, known events and sound signatures can be verified by customer service, technical support, clinicians, marketing specialists, or research and development staff.

In some embodiments, a speaker of the hemodialysis machine can emit an audio prompt to the user. For example, the detection device can transmit a signal to the hemodialysis machine, causing the speaker of the hemodialysis machine to emit an audio prompt. For example, the hemodialysis machine can emit an audio prompt to the patient, a care-partner, or a clinician using the speaker to request more information from the patient or clinician to identify whether the system is in pretreatment (e.g., setting up for treatment), mid treatment, or post treatment. The hemodialysis machine can emit an audio prompt to the patient, a care-partner, or a clinician to reboot the system or to run a diagnostic. The hemodialysis machine can also emit an audio prompt to the patient, a care-partner, or a clinician to run a diagnostic after treatment is finished.

In some embodiments, a patient can manually upload sound signatures using a detection device. For example, a patient can use a smartphone app (e.g., the Fresenius "My Companion" patient app) to record and submit a sound signature to the server. The server can then process the sound signature as described above. This can be useful if a patient identifies an irregular noise during treatment.

In some embodiments, a cloud based voice orchestration platform can be used to distribute or publish the sound signatures or communicate between the detection devices and the servers. Also, the detection device can communicate with the server through one or more hardwire connections (e.g., serial cable, parallel cable, etc.). Wireless techniques such as infrared (IR), radio frequency (RF), Bluetooth, wireless Ethernet, or other electromagnetic linking techniques, may also be used. One or more protocols, transmission standards, and data formats may also be used for passing information between the detection device and the server.

In some embodiments, storing a predetermined sound signature can include storing additional data about the sound signature, including but not limited to: a timestamp of occurrence, an identification of the medical treatment device, and/or a location of occurrence.

While the detection devices and servers above have been described as being part of PD systems and hemodialysis systems, these types of devices can be used in any of various other types of medical systems and medical fluid pumping systems. Some examples of medical systems include vital measurement devices, fluid heaters, and other systems with fluid lines. Other examples of medical fluid pumping systems in which the devices and servers described herein can be used include hemofiltration systems, hemodiafiltration systems, apheresis systems, and infusion pump systems.

What is claimed is:

1. A method of monitoring a medical treatment device, the method comprising:

detecting a sound of the medical treatment device with a detection device;

determining, via a processor of the detection device, whether a sound signature of the sound matches a predetermined sound signature;

determining, via the processor of the detection device, a phase of treatment of the medical treatment device out of a group of phases comprising pretreatment, mid-treatment, and posttreatment;

upon a determination by the processor of the detection device that (i) the sound signature matches the predetermined sound signature and (ii) the phase of treatment is a first phase of treatment, automatically causing the medical treatment device to deploy a first intervention out of a group of first interventions comprising running a diagnostic on the medical treatment device, rebooting the medical treatment device, and stopping a treatment of the medical treatment device, and upon a determination by the processor of the detection device that (i) the sound signature matches the predetermined sound signature and (ii) the phase of treatment is a second phase of treatment, automatically causing the medical treatment device to deploy a second intervention out of a group of second interventions comprising running a diagnostic on the medical treatment device, rebooting the medical treatment device, and stopping the treatment of the medical treatment device, wherein the first phase of treatment is different than the second phase of treatment, and the first intervention is different than the second intervention.

2. The method of claim 1, wherein the first and second group of interventions comprise displaying a notification.

3. The method of claim 2, wherein the notification is a push notification on a smartphone.

4. The method of claim 1, wherein the first and second groups of interventions comprise initiating an audio prompt on a device associated with a patient of the medical treatment device.

5. The method of claim 1, wherein the first and second groups of interventions comprise initiating a phone call to a phone associated with a patient of the medical treatment device.

6. The method of claim 1, wherein the first and second groups of interventions comprise initiating an audio prompt on a device associated with a patient and/or clinician of the medical treatment device to reboot the medical treatment device.

7. The method of claim 6, wherein the first and second groups of interventions comprise initiating the audio prompt on the device associated with the patient and/or clinician to reboot the medical treatment device after determining that the medical treatment device is in a pretreatment phase.

8. The method of claim 7, wherein the predetermined sound signature is associated with a pump of the medical treatment device.

9. The method of claim 1, wherein determining that the sound signature matches the predetermined sound signature comprises comparing the sound signature to sample sound signatures stored in a database.

10. The method of claim 9, wherein the sample sound signatures are uploaded to the database and identified through machine learning.

11. The method of claim 1, wherein the predetermined sound signature is indicative of a malfunction of the medical treatment device.

12. The method of claim 11, wherein the predetermined sound signature is indicative of a venous disconnect.

13. The method of claim 11, wherein the predetermined sound signature is indicative of a pump malfunction.

14. The method of claim 1, wherein the medical treatment device is a hemodialysis machine.

15. The method of claim 1, wherein the medical treatment device is a peritoneal dialysis machine.

16. A medical treatment system comprising:

a medical treatment device;

a detection device configured to detect a sound of the medical treatment device, wherein a processor of the detection device is configured to:

determine whether a sound signature of the sound matches a predetermined sound signature;

determine a phase of treatment of the medical treatment device out of a group of phases comprising pretreatment, mid-treatment, and posttreatment;

upon a determination by the processor of the detection device that (i) the sound signature matches the predetermined sound signature and (ii) the phase of treatment is a first phase of treatment, automatically cause the medical treatment device to deploy a first intervention out of a group of first interventions comprising running a diagnostic on the medical treatment device, rebooting the medical treatment device, and stopping a treatment of the medical treatment device, and upon a determination by the processor of the detection device that (i) the sound signature matches the predetermined sound signature and (ii) the phase of treatment is a second phase of treatment, automatically cause the medical treatment device to deploy a second intervention out of a group of second interventions comprising running a diagnostic on the medical treatment device, rebooting the medical treatment device, and stopping the treatment of the medical treatment device, wherein the first phase of treatment is different than the second phase of treatment, and the first intervention is different than the second intervention.

17. The medical treatment system of claim 16, wherein the first and second group of interventions comprise initiating an audio prompt on a device associated with a patient of the medical treatment device to reboot the medical treatment device.

18. The medical treatment system of claim 16, wherein the detection device comprises a microphone.

19. The medical treatment system of claim 16, wherein the processor is configured to determine whether the sound signature matches the predetermined sound by comparing the sound signature to a database of sample sound signatures.

20. The medical treatment system of claim 16, wherein the predetermined sound signature is indicative of a malfunction of the medical treatment device.

21. The medical treatment system of claim 20, wherein the predetermined sound signature is indicative of a venous disconnect.

22. The medical treatment system of claim 20, wherein the predetermined sound signature is indicative of a pump malfunction.

23. The medical treatment system of claim 20, wherein the predetermined sound signature is a rattling of a housing of the medical treatment device.

* * * * *